(12) United States Patent
Girndt

(10) Patent No.: US 7,293,461 B1
(45) Date of Patent: Nov. 13, 2007

(54) ULTRASONIC TUBULARS INSPECTION DEVICE

(76) Inventor: Richard Girndt, 5144 Castlebrook, Spring, TX (US) 77389

( * ) Notice: Subject to any disclaimer, the term of this patent is extended or adjusted under 35 U.S.C. 154(b) by 84 days.

(21) Appl. No.: 10/971,860

(22) Filed: Oct. 22, 2004

Related U.S. Application Data

(60) Provisional application No. 60/481,540, filed on Oct. 22, 2003.

(51) Int. Cl.
*G01N 29/24* (2006.01)

(52) U.S. Cl. ............................ 73/622; 73/628; 310/336

(58) Field of Classification Search ................... 73/622, 73/628; 310/336
See application file for complete search history.

(56) References Cited

U.S. PATENT DOCUMENTS

| | | |
|---|---|---|
| 4,020,688 A | 5/1977 | Hauldren |
| 4,106,347 A | 8/1978 | DeKerlegand |
| 4,195,530 A | 4/1980 | Ross et al. |
| 4,217,782 A | 8/1980 | Pont |
| 4,319,490 A | 3/1982 | Hartmann, Jr. |
| 4,404,853 A | 9/1983 | Livingston |
| 4,487,072 A | 12/1984 | Livingston |
| 4,718,277 A | 1/1988 | Glascock |
| 5,313,837 A | 5/1994 | Haynes |
| 5,600,069 A | 2/1997 | Girndt et al. |

OTHER PUBLICATIONS

Ultrasonic Testing of Tube-Phased Array Technique-No Mechanical Rotation, Sep. 26, 2003###.
Piezocompsite Transducers-a Milestone for Ultrasonic Testing; G. Splitt, NDTnet, Jul. 1996, vol. 1, No. 07.
First Results of Composite Transducers Used in Automatic Rotating Ultrasonic Inspection Units, Dr.-Eng. Roman Koch, NDT.net-Oct. 2002, vol. 2, No. 10.
Improvements of Ultrasonic Inspections Through the Use of Piezo-Composite Transducers, Gerard Fleury, Christian Gondard-6th European Conference on Non Destructive Testing, May 1995.
Use of Flexible Ultrasonic Arrays in Inspection; Jocelyn Langlois, NDT.net, Mar. 1999, vol. 4, No. 3.

*Primary Examiner*—John E. Chapman
(74) *Attorney, Agent, or Firm*—Fulbright & Jaworski LLP

(57) ABSTRACT

A system, method, and apparatus for ultrasonic detection of flaws or defects in oil field tubulars utilizing composite transducers. An array of composite transducers are utilized to detect anomalies in the tubulars, such as transverse, wall or longitudinal defects. The use of the composite transducers allow for a greater inspection area over traditional transducers thereby reducing the number of channels needed for inspection of the tubulars.

29 Claims, 11 Drawing Sheets

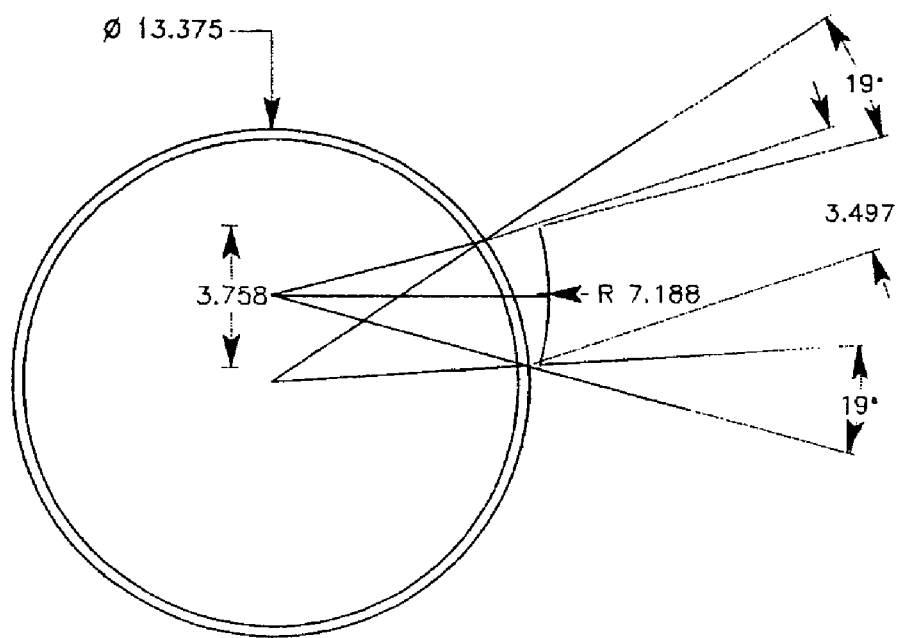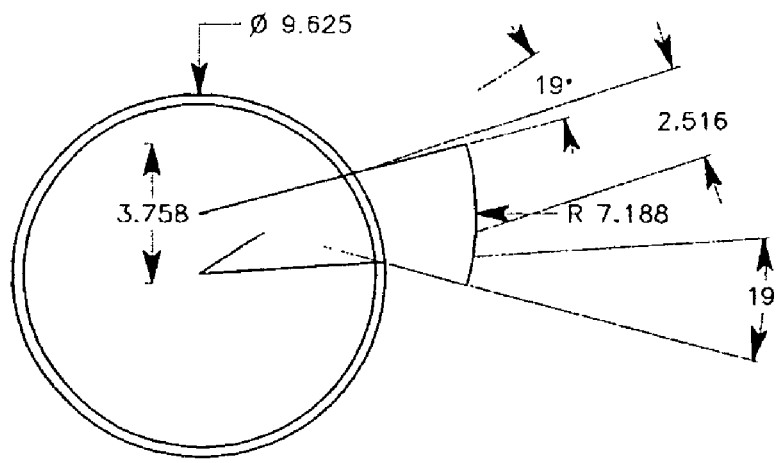
FIG. 9

ULTRASONIC TUBULARS INSPECTION DEVICE

This application claims priority to U.S. provisional application 60/481,540, filed Oct. 22, 2003.

TECHNICAL FIELD

The present invention relates to a system, method and apparatus for the detection of flaws or defects in oil field tubulars. More particularly, the present invention relates to a system, method, and apparatus for ultrasonic detection of flaws or defects in oil field tubulars utilizing composite transducers.

BACKGROUND OF THE INVENTION

Current tube inspection technology utilizing ultrasonic technology consists of units of three distinct types: 1) rotating head, 2) tube rotates in place, head traverses the length of the tube, and 3) helical advance—canted roller scheme. All three of these methods are restricted by certain constants inherent to the use of ultrasound as a testing medium on all types of products, equipment, and structures.

Few industries require ultrasonic inspection at higher speeds, with greater accuracy than in the inspection of oilfield tubulars such as tubing, casing, and drill pipe. The required speeds and the constant quest to increase the speeds are driven by competitive pressure, steel mill production rates, and the desire to lower manufacturing costs which in turn increase profits.

An article titled "Ultrasonic Testing of Tube—Phased Array Technique" co-sponsored by NDT Systems of France and Sandvik Steel AB of Sweden, goes into extensive detail regarding the inherent problems and shortcomings of current tube testing technology as well as the merits of encircling a tubular product with ultrasonic probes. The co-authors have identified the fairly new technology of phased array ultrasound as the best, cost effective approach to accomplish full body ultrasonic inspection without the use of rotating ultrasonic probes.

In fact, commercially available, non-rotating, phased array tube testing systems are currently operating in production environments at pipe manufacturing facilities. Phased array technology is widely viewed by the next technological leap in the tube testing industry.

It is important to note that the aforementioned reference, published in 1996, has a defined set of "application fields," but it can be seen that the focus for the end use of the proposed development is the nuclear field, where pipe diameters requiring critical NDT inspections tend to be much smaller than of the most commonly inspected products in the Oil Country Tubular Goods (OCTG) field, which commonly exceed 40 feet in length and whose diameters range from 2 ⅜" through 20" and beyond. The reference comments on the known competition in 1996, in which "everybody is working according to conventional technologies: this means single element probes, rotating mechanically around the tube with very complex and expensive systems." The reference also comments on a specific company called "Nukem." This company is known to specialize in the inspection of smaller diameter tubes at high speeds. Indeed, it can be reasoned that future development is focused on using the costly phased array method to ultrasonically inspect tubular products.

In addition to the rotating probe approach, also outlined herein are the helical advance conveyor system, the overhead gantry approach, and now the introduction of phased array transducers encircling the pipe as commonly known and accepted approaches to OCTG inspection. It should be noted that these mechanical or technological approaches to ultrasonic tube inspection apply not only to the oil industry, but wherever a cylindrical object may be considered for ultrasonic NDT.

What is unique to the ultrasonic inspection of OCTG is the large surface area needing inspection, coupled with the need for high production rates, which in turn require greater and greater numbers of ultrasonic channels to achieve these goals. The article "Ultrasonic Testing of Tube—Phased Array Technique" describes an electronics data management system to handle between 1000 and 2000 individual ultrasonic transducers.

Currently marketed phased array inspection systems for OCTG, require far more than the contemplated one to two thousand channels, if the systems are to comply with American Petroleum Institute (API) or end user customer specifications for casing and tubing inspection, that require at a minimum, inspection for longitudinal, transverse, and wall thickness abnormalities or flaws. In fact, phased array transducers, covering less than two inches of longitudinal or transverse surface area, can contain up to 256 individual elements and individual channels.

To achieve axial inspection of tubulars without rotation of the tube or test transducers, by definition, the ultrasonic probes must encircle the pipe as contemplated and in use in current phased array systems. Also for minimum inspection requirements acceptable on OCTG, that inspection coverage may require wall thickness measurement as well as transverse and longitudinal flaw inspection. Furthermore, the inspection for longitudinal and transversely oriented flaws, using ultrasonic shear waves, should be conducted from both the leading and trailing sides of a transversely oriented flaw and the counter and counter-clockwise sides of a longitudinal flaw.

Many advances in OCTG ultrasonic inspection have taken place since the first commercialization of the technology in the mid seventies. Now computer controlled digital electronics components allow for higher pulse repetition rates, greater numbers of channels, and wide latitude in the collection and dissemination of the resultant data. Further advances have been made in the manufacture of ultrasonic transducers with the most common types being made of quartz or ceramic materials as outlined and identified in U.S. Pat. No. 4,404,853 to Livingston.

More recently, much research has been done with piezocomposite materials for the manufacture of ultrasonic transducers. In the July 1996 Article "Piezocomposite Transducers—A Milestone for Ultrasonic Testing" by Dr. Gerald Splitt, numerous advantages realized through the use of composite transducers are discussed, including lower signal to noise ratio, high acoustic efficiency, low acoustic impedance, and lower amplifier gain among others. This article is incorporated by reference herein for all purposes. Of greater importance to the present invention has to do with the method of manufacturing composite sheets that are in turn finished to final transducer element characteristics. Notably, this method described makes it possible to fabricate piezocomposite plates with dimensions of 50×50 mm square or bigger, which are used to produce multiple transducers of smaller size by known methods as mechanical or laser cutting or dicing. Also of note is that piezocomposite can be bent into a cylindrical or spherical shape. This allows one to build line or point focus transducers without the need for an additional lens in front of a crystal. The reference further comments that for arrays and paintbrush probes the construction with piezocomposite transducers becomes substantially easier as here only a light backing is needed to produce high resolution probes.

Those familiar with automated ultrasonic testing will recognize the terms line focus, point focus, arrays, and paintbrush probes as they relate to ultrasonic transducers, and will further recognize the difference between these commonly known probe types and the curved piezocomposite probes outlined and used in the proposed invention.

An additional technical paper of note is "First Results Of Composite Transducers Used in Automatic Rotating Ultrasonic Inspection Units," authored by Dr Roman Koch and presented in June 2002. This paper goes into much detail regarding actual field testing of composite transducers in automated tube testing machines, specifically the rotating probe method mentioned previously. The article speaks to the aforementioned advantages of piezocomposite probes over conventional transducer elements but is of importance in this case as it relates directly to tube testing. The development of piezocomposite materials for ultrasonic transducers in the middle of the nineties first for the medical probes and then for the standard contact probes gave us the change also to optimize the probes of automatic ultrasonic testing machines to improve the defect sensitivity and resolution. This statement confirms the history of composite probes as well as their short period of use in industrial tube testing applications. The paper goes on to explain in detail the optimization of the sound field and reduction of the lens losses when curving the composite material itself. Again, as in previously referenced articles, the curving addressed is for the sole purpose of focusing the sound beam by curving the composite material in order to improve on inherent shortcomings of using a lens to perform the focusing function. Also of note is the statement that in automated ultrasonic testing systems that in such units often array probes are used where the crystal of the probe is divided in several individual elements, which are connected to individual electronic evaluation channels, to increase testing speed. The use of transducers in combination to increase coverage and speed will be discussed later in detail to point out the advantages of the present inventions improvement over current techniques as well as to draw attention to the uniqueness of the present invention.

BRIEF SUMMARY OF THE INVENTION

The present invention relates to a system, method and apparatus for the detection of flaws or defects in oil field tubulars. More particularly, the present invention relates to a system, method, and apparatus for ultrasonic detection of flaws or defects in oil field tubulars utilizing curved composite transducers.

A system, method, and apparatus for ultrasonic detection of flaws or defects in oil field tubulars utilizing curved composite transducers. An array of curved composite transducers are utilized to detect anomalies in the tubulars, such as transverse, wall or longitudinal defects. The use of the composite transducers allow for a greater inspection area over traditional transducers thereby reducing the number of channels needed for inspection of the tubulars.

The scope of the present invention involves using the large sheets of composite material mentioned in the referenced article "Piezocomposite Transducers—A Milestone for Ultrasonic Testing," not to produce numerous small individual composite transducers, curved to replace a conventional focusing lens, but to produce much larger probes, up to three inches and above, where the entire large single element is curved to a set radius as opposed to the much documented practice of curving smaller elements for focusing purposes. Unlike conventional transducer piezoelectric materials, the new composites can be shaped over a large area while still maintaining the effective beam properties required to insure 100% coverage, while maintaining sensitivity to the detection of small flaws as is required in OCTG inspection. These properties are desired for the present invention: a) uniform beam characteristics, b) equal sensitivity over the entire face of the composite probe, c) the ability to produce transducers with a smaller radius than previously possible, and d) the ability to curve a large sheet of composite material to make a single element probe with unique properties critical to the current invention as opposed to the common practice of curving numerous smaller elements and using them in an array to provide coverage and speed in tube inspection.

The present invention utilizes probes or transducers that work in all three of the previously defined defect detection minimum requirements, namely longitudinal, transverse, and wall thickness measurement. The method and advantages of each type of inspection is discussed in detail in the following text and drawings.

In one aspect of the invention there is a method for ultrasonic inspection of tubulars. The method includes providing a first circular array of composite transducers, said transducers having a proximate curved surface; passing a tubular past said first array, said tubular having an outer peripheral surface; and inspecting for abnormalities in the tubular utilizing said transducers. The step of passing includes moving the tubular in a longitudinal direction past said first array without rotating the tubular in a circumferential direction. The step of providing includes maintaining said first array in a stationary position.

The inspecting step may include determining abnormalities of a longitudinal flaw type, determining abnormalities of a transverse flaw type, and/or determining abnormalities in the wall thickness.

The inspecting step may include utilizing shear waves for determining abnormalities of a longitudinal flaw type and transverse flaw type.

The transducers may be of various radii and length. For example, the transducers may each be a length of greater than 2 inches. Additionally, the transducers are each a length of between 0.25 inches and 2 inches. The transducers may be sized appropriately for the particular OD of the tubular being inspected.

In one aspect of the method, the passing step includes maintaining the proximate curved surface of each transducer equidistant from said outer peripheral surface of the tubular.

In another aspect of the method, the outer peripheral surface of the tubular has a radii of curvature, and said proximate curved surface of the transducer has a radii of curvature greater than the radii of curvature of the outer peripheral surface. The proximate curved surface is the surface of the transducer directed at the tubular during ultrasonic inspection.

In another aspect of the invention, the method includes the step of providing a second and third array of composite transducers, said transducers having a proximate curved surface. Relative to a central longitudinal axis of the tubular, the transducers of the second and third array are angled 19 degrees in water to produce a 45 degree refracted angle. The inspecting step includes determining abnormalities of a transverse flaw type.

In one embodiment, the second and third array each includes eight transducers. Different number of composite transducers may be utilized.

In one aspect of the invention, the tubular (or pipe) has a diameter ranging equal to or greater than about 2 ⅜ inches. Although, the diameter of the inspected pipe is not limited to that range, the inventive system and method allow for inspection of larger diameter pipe with fewer channels.

In one aspect of the invention there is the step of providing a phased array longitudinal inspection system having individual phased array channels aligned to form a radius.

In another aspect of the invention, there is the step of providing a fourth and fifth array of composite transducers. The transducers of the fourth and fifth array having a proximate curved surface, the fourth and fifth array adapted to inspect for longitudinal flaws.

The invention also includes an improved system for ultrasonic inspection of tubulars. In one embodiment of the inventive system, there is a first circular array of composite transducers. The transducers have a proximate curved surface and the circular array is adapted for inspecting for abnormalities in a tubular utilizing said transducers.

In another aspect of the system, the system. includes a phased array longitudinal inspection system having individual phased array channels with multiple elements.

In another aspect of the system, the system includes a second and third array of composite transducers. The transducers have a proximate curved surface that is angled toward a tubular being inspected. The second and third array are angled 19 degrees in water to produce a 45 degree refracted angle. The second and third array are adapted to inspect for abnormalities of the transverse flaw type.

The system include a fourth and fifth array of composite transducers. The transducers of the fourth and fifth array having a proximate curved surface adapted to inspect for longitudinal flaws.

In one aspect of the invention, the first array is adapted to inspect for variations in wall thickness.

The method and system of the present invention, may utilize varying length and radii for inspection of tubulars. The tubulars include oil field tubulars such as drill pipe, but may also include other types of tubulars for inspection. The number of channels needed to inspect tubulars is reduced over prior art inspection systems because of the ability of the composite transducer to provide a much larger inspection area.

The transducers may be maintained at a fixed position while maintaining 100% coverage on increasingly smaller diameters of tubulars thereby increasing the water path to the surface of the tubular with no mechanical change over required.

The foregoing has outlined rather broadly the features and technical advantages of the present invention in order that the detailed description of the invention that follows may be better understood. Additional features. and advantages of the invention is described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages is better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 9 is a drawing illustrating an embodiment of a curved composite transducer can be developed for a range of tubular diameters;

DETAILED DESCRIPTION OF THE INVENTION

Figure 1:
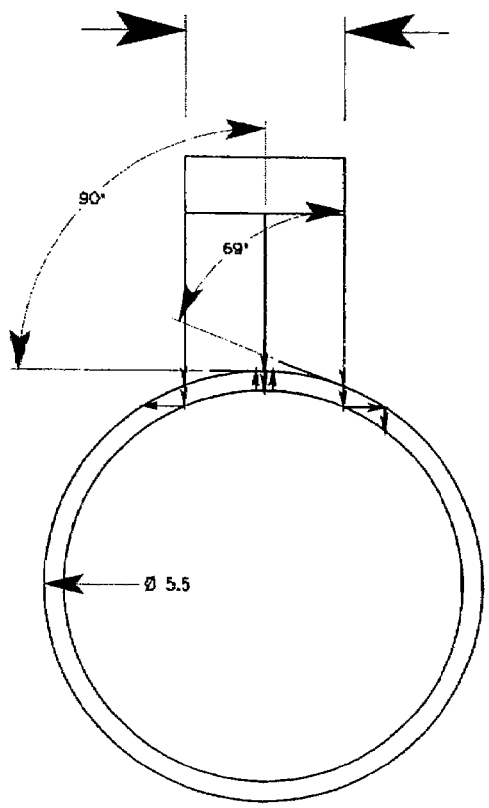
FIG. 1 is a drawing illustrating problems associated with using a long conventional transducer element for taking ultrasonic wall thickness measurements.

As used herein, the term "a" or "an" may mean one or more. As used herein in the claim(s), when used in conjunction with the word "comprising", the words "a" or "an" may mean one or more than one. As used herein, "another" may mean at least a second or more.

As used herein, the term "surface speed" means the actual speed of the tubular surface as it passes the face of an ultrasonic transducer. Expressed in inches per second (ips).

As used herein, the term "pulse repetition rate" means the number of times per second an ultrasonic transducer is electronically pulsed, resulting in. a sound wave of definable parameters expressed in kilohertz (e.g. 2400 pulses per second=2.4 kilohertz).

As used. herein, the term "pulse gap" means the distance between successive "pulses" of a transducer on the surface of the tubular being inspected. Calculated by dividing the surface speed in inches per second by the pulse repetition expressed in thousands (e.g. 2.4 Khz-2400).

As used herein, the term "effective beam" means the usable portion of the face of the ultrasonic transducer expressed in thousandths (i.e. transducer crystal 0.500" times 70% effective beam width=0.350").

As used herein, the term "pipe diameter" means the outside or external diameter of the tubular being inspected.

As used herein, the term "helical advance" means the distance an oilfield tubular advances, expressed in inches, relative to a fixed set of ultrasonic transducers, for each rotation of the tube or ultrasonic head.

As used herein, the term "transducers per array" means the number of individual transducer elements, used in conjunction as a sum of individual effective beams, to form an area of 100% coverage at the surface of the tubular being tested.

As used herein, the term "tube length" means the overall axial length, from the leading to the trailing edge of the tubular being inspected expressed in feet.

As used herein, the term "cost per ultrasonic channel" means the average cost per channel for the multi-channel ultrasonic instrumentation required to pulse the individual transducers, and in turn, the arrays.

As used herein, the term "forward advance" means the product of the resultant revolutions per minute and the helical advance, based on not exceeding the assumed constants.

The present invention, designed to meet the American Petroleum Institutes (API's) Specification 5CT for the detection of longitudinal, transverse, and wall thickness anomalies or defects in Oil Country Tubular Goods (OCTG) using the ultrasonic method, seeks to greatly increase the throughput speeds, while simultaneously reducing the cost of the system by reducing the number of ultrasonic channels needed to achieve 100% coverage, and making the system a non-contact style (the shoes and/or transducers do not touch the pipe which minimizes wear), leading to less maintenance.

Wall Thickness Inspection

Certain drawings referred to herein depict the difference between conventional ultrasonic probes and the curved composites used in the current invention, both from a practicality standpoint and the associated. cost benefits.

FIG. 1 depicts the problems associated with using a long conventional transducer element for taking ultrasonic wall thickness measurednts. It can be seen that the sound emitted from the center of the transducer strikes the tube perpendicular (90 degrees) to the surface, which is a requirement for compression wave wall thickness readings, while the beam from the outer edges strikes the pipe surface at an incident angle of 69 degrees to the tangent of the circle, which would result in no return of signal for wall measurement, as shear waves would be induced in the part at the outer edges of the probe.

Figure 2:
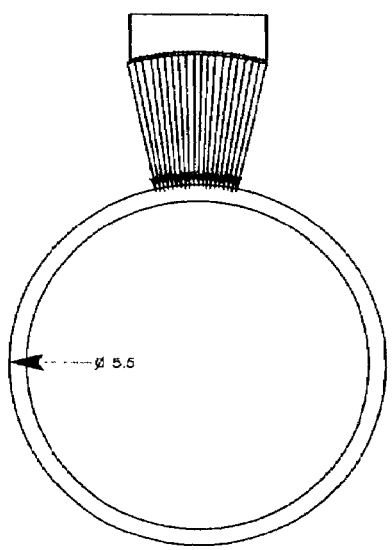
FIG. 2 is a drawing illustrating how to overcome the restrictions of using a large flat element for wall thickness measurements by using multiple individual elements, or arrays, arranged in a curved case equidistant from the curved surface.

FIG. 2 shows how to overcome the restrictions of using a large flat element for wall thickness measurements by using multiple individual elements, or arrays, arranged in a curved case equidistant from the curved surface. This is commonly done with conventional, composite, and newer phased array systems, though it is apparent to anyone versed in the art that the cost associated not only with the individual elements but to a larger degree, the individual ultrasonic channels required to pulse the multiple elements, that this method pales in comparison to the potential to use a single element, though as we have shown, standard flat transducers will not work for this application.

It is important to realize that the use of the proposed curved composite probe methodology for wall thickness measurement is on its own merits a viable and valuable invention and product. The measurement of wall thickness with ultrasound is commonly accepted as the most accurate measurement system currently in use. A unique property of ultrasonic wall thickness measurement is that to a large degree, increasing the distance from the transducer face to the surface of the part being inspected does not detract from the accuracy of the measurements taken.

Figure 3:
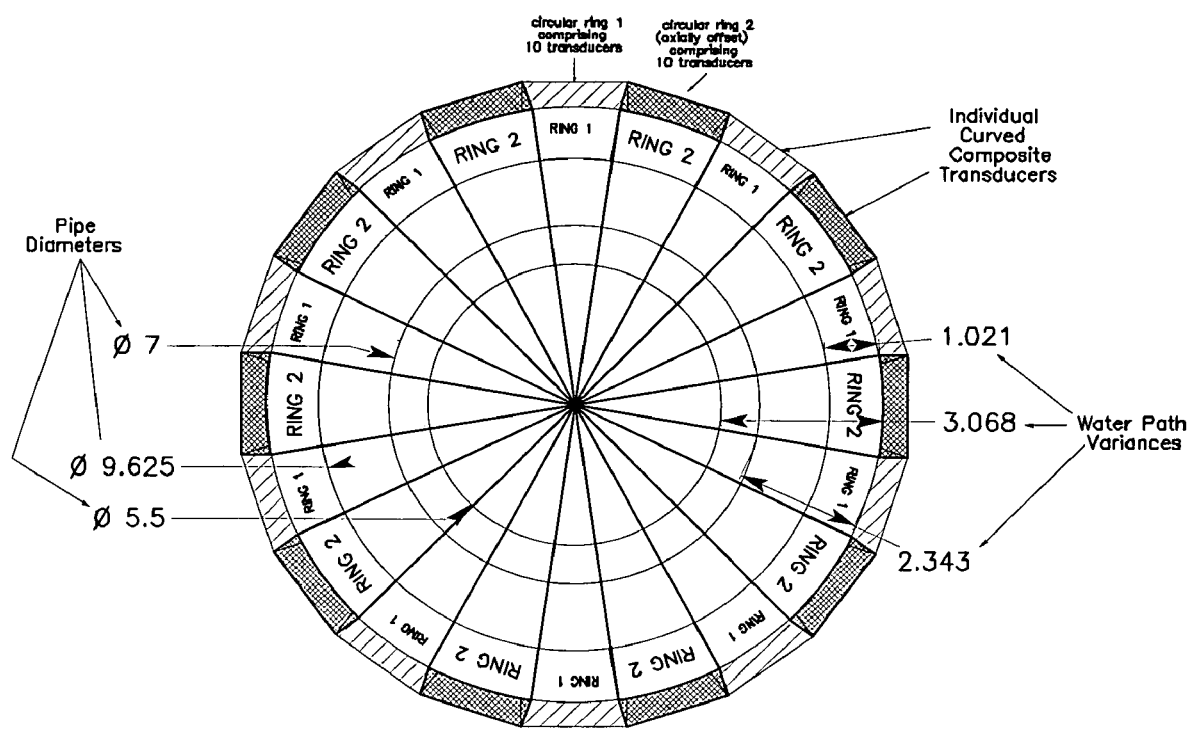
FIG. 3 is a drawing illustrating an embodiment of the use of curved composite probes contemplated in the present invention.

As demonstrated in FIG. 3, the use of the curved composite probes contemplated in the present invention not only lend themselves to the testing of multiple diameter tubulars, but in fact when the curvature is designed for 100% coverage of the larger diameter range, and the selected transducer radius is slightly larger than the largest diameter to be inspected for wall thickness, the increase of the water path or delay line also insures 100%+coverage on subsequent smaller diameters passed through the fixed circular array without the necessity of changing the probes or their position relative to the center of the circle. This is possible because the incident angle for wall thickness inspection is perpendicular to the tubular being tested and the relative movement closer or further from the test specimen does not alter this angle of incidence. The ability to inspect for wall thickness in this manner reduces changeover time for varying diameters of tubes and guarantees full coverage over a range of diameters. This is of particular importance given upcoming changes to API specifications (already in draft form) in the area of Product Specification Levels (PSL's) that may require 100% wall coverage on tubulars historically inspected with the gamma wall source found on electromagnetic (EMI) tube inspection units. This feature of the current invention makes the wall inspection component viable as a replacement for current gamma wall measurement systems, in use worldwide, and well know to those familiar with the currently available technology.

Transverse Flaw Inspection

In the case of transverse flaw inspection, the same curved composite probes envisioned above would entail two additional sets of probes of similar physical dimensions as depicted in FIG. 3, though the transverse flaw inspection portion would entail two rings of transducers, one leading and one trailing, angled 19 degrees in water to produce a 45 degree refracted angle, pointing down the axis of the pipe with the sound beams directed at the two respective pipe ends.

Figure 4:
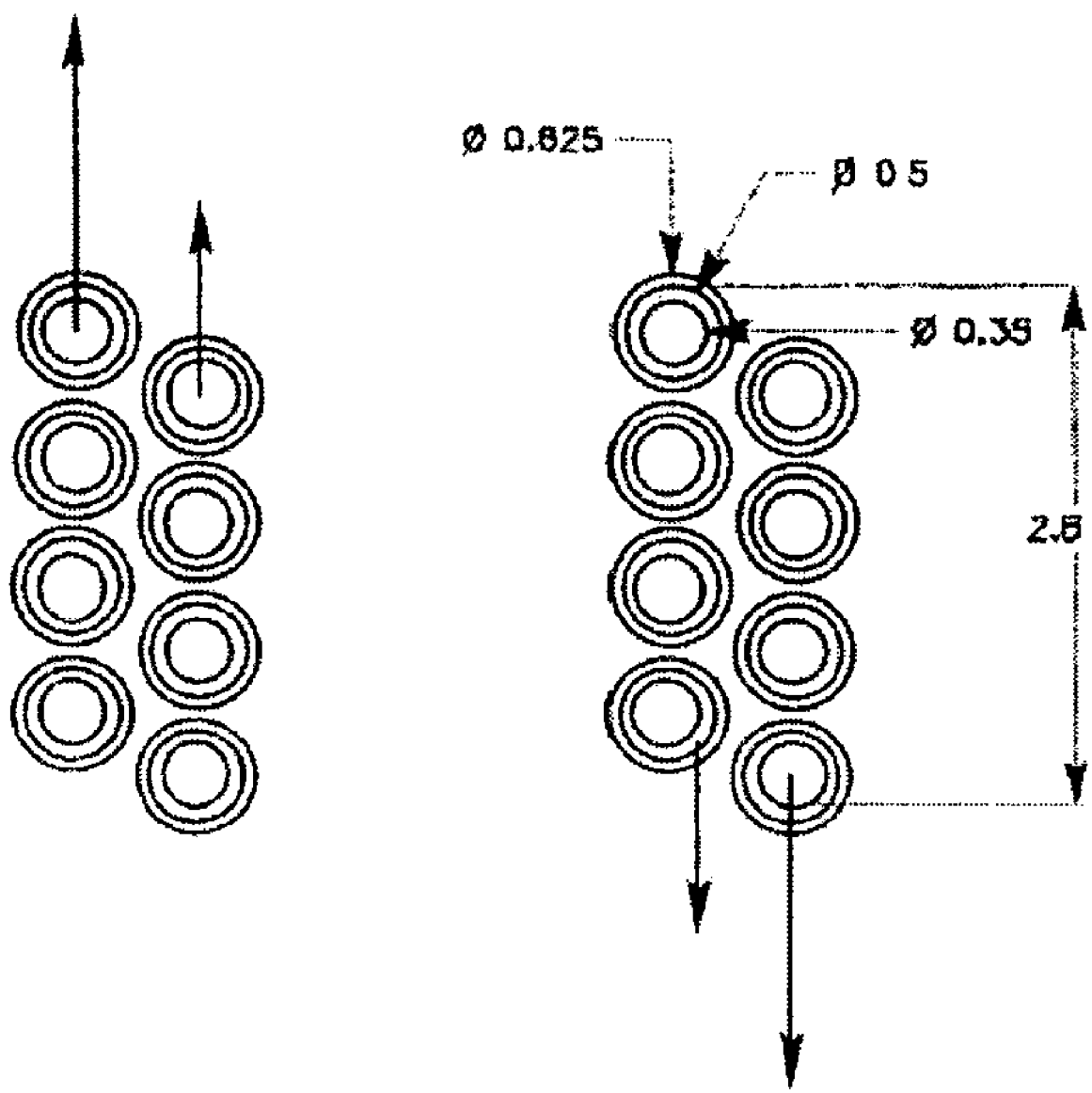
FIG. 4 is a drawing illustrating the current methodology of using multiple transducers in tandem, as a collection of overlapping effective beams.

FIG. 4 depicts the current methodology of using multiple transducers in tandem, as a collection of overlapping effective beams, to produce 100% coverage at, in this depiction, a potential 2.8" helix per revolution. In other words for each revolution of a pipe the set of transducers can move forward 2.873" (helical advance). The leading end of the transverse array is shown on the left and the trailing end of the transverse array is shown on the right. Transducer elements having a 0.500" diameter are shown, each transducer element encased in a 0.625" diameter case and having an effective beam 0.35" in diameter. The solid arrows shown projecting from the transducer array indicate the direction of the combined ultrasonic beam. To detect transverse flaws, the prior art transducer array utilizes eight 0.500 inch element transducers with an approximate 2.8 inch coverage. (Calculated by 0.625" transducer case–0.500" transducer element–0.350" effective beam times 8 transducers=2.8" array).

Figure 5:
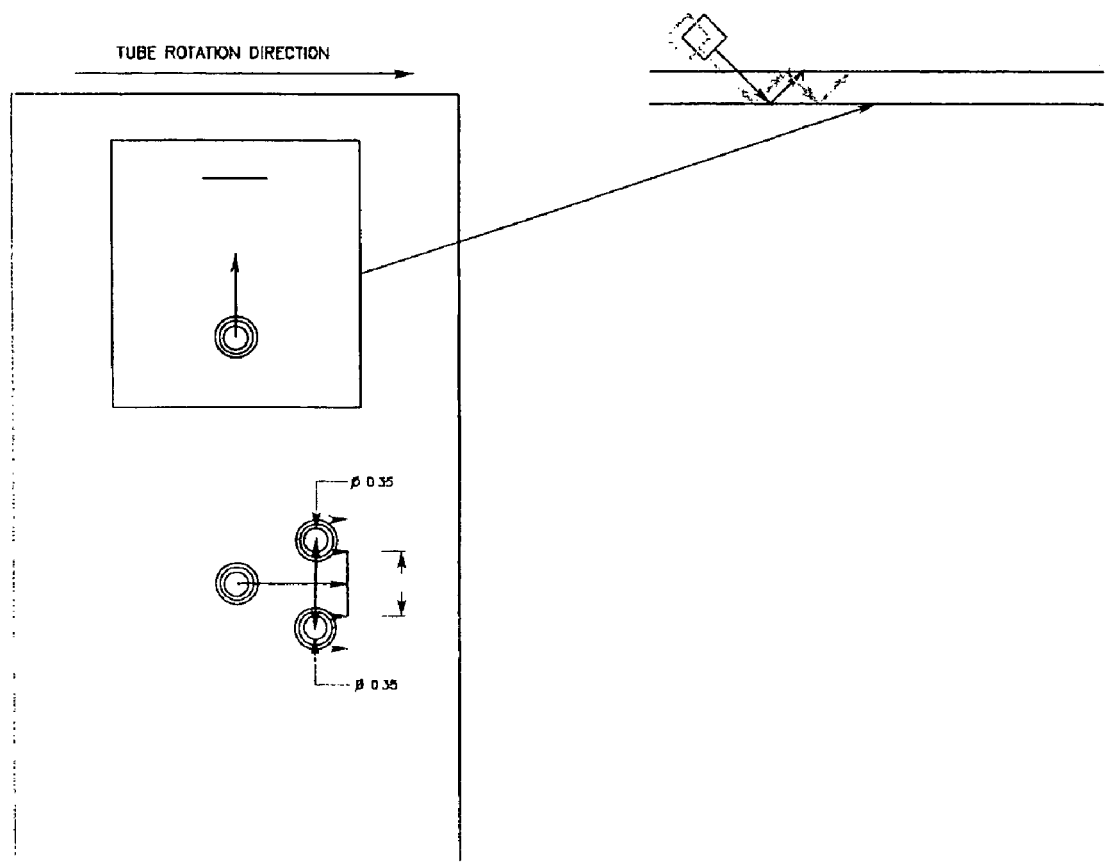
FIG. 5 is a drawing illustrating a problem common to inspection for transverse flaws from an ease and consistency of detection perspective.

FIG. 5 illustrates a problem common to inspection for transverse flaws from an ease and consistency of detection perspective. The top portion of FIG. 5 illustrates a transverse transducer and the direction of its effective beam (indicated by the solid arrow projecting axially). A longitudinal transducer and the direction of its effective beam are illustrated directly below the transverse transducer. The distance from the effective beam to the flaw (illustrated as a horizontal line above the transverse transducer) can vary only slightly without an adverse impact on the probability of detection. Where the longitudinal transducer can have an axial displacement of up to 1" and still detect the longitudinal flaw with the effective beam, the transverse transducer with only slight axial movement either misses detection of the flaw, or results in an amplitude decrease which would result in the signal falling below pre-established alarm thresholds.

In the current invention, this obstacle is of course negated with the tubular traveling axially past a fixed curved transducer. This phenomenon is briefly mentioned in the previously referenced article "First Results Of Composite Transducers Used in Automatic Rotating Ultrasonic Inspection Units," where discussing the results of sensitivity during a transversal-test as follows: Here, the sensitivity is poor for standard probes due to the small pulse response caused by the reason that the focal line is perpendicular to the defect orientation to fulfill 100% coverage. The article discusses that this is caused by the improvement of bandwidth and additionally by the influence of the optimized sound field of the piezocomposite probe by curving the material itself. As previously discussed, the curving is specific to small individual probes used in an array of the type depicted in FIG. 4 above, and does not consider the curving of a large single element to replace this entire array, as is the focus of the present invention.

Figure 6:
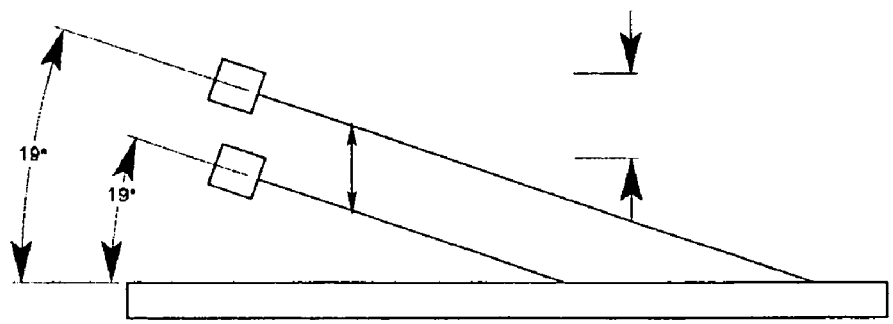
FIG. 6 is a drawing illustrating that during transverse flaw inspection when moving a transducer closer or further from the surface of the part being inspected does not alter the incident inspection angle.

As with the wall thickness inspection component depicted in FIG. 3, when performing transverse flaw inspection, moving the transducer closer or further from the surface of the part being inspected does not alter the incident inspection angle as shown in FIG. 6.

This ability to sustain movement closer or further from the pipe surface without impacting the incident inspection angle is common only to the transverse and wall thickness inspection methods and does not apply to the ultrasonic inspection for longitudinally oriented flaws, as discussed in greater detail in the following section.

Of merit however, is that just as the wall thickness component of the proposed invention has commercial applications as a stand alone inspection device, when the wall system is coupled with the transverse inspection component, a far superior method for the inspection of used drill pipe, which requires only transverse and wall thickness inspection, can be realized.

The most common methodology in use today for the inspection of used drill pipe is a multi-part inspection, but for the purpose of the proposed embodiment, only the tube body and critical (slip) end area inspections are considered and discussed. In the inspection of used drill pipe, an electromagnetic "buggy," is run down the tube body for the detection of transversely oriented defects or fatigue cracks, which can be formed due to the stresses involved in the drilling process. This technology has not changed significantly in decades and is time consuming and does not offer the superior detection possibilities associated with ultrasonic inspection. For more critical applications, a secondary inspection is often incorporated, using the ultrasonic method to locate transverse flaws in the slip area of the drill pipe tube. This scanning is currently performed by hand with either a single probe affixed to a wedge, or through the use of a commercially available, hand held device with the ultrasonic transducers mounted in a fluid filled wheel that traverses the area of interest at a fixed helical advance, while the tube is rotated in place. Both these methods are time consuming and labor intensive, making this a costly, albeit necessary inspection on used drill pipe. By combining the wall thickness and transverse components of the current invention, and traversing the drill pipe through a water filled "stuffing" box, or as mentioned later, alternate coupling means such as lucite/rexolite wedges fluid filled wheels to name examples, common to those versed in the industry, it is possible not only to achieve a more critical ultrasonic inspection of the tube body but at the same time and in a single pass, inspect the critical end area and negate the need for a costly, labor intensive, secondary inspection of this critical area.

Figure 7:
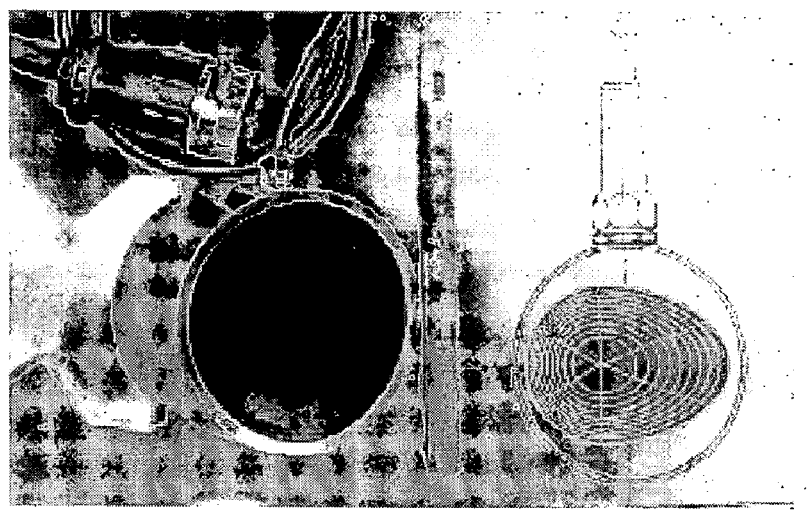
FIG. 7 is a drawing illustrating a multitude of transducer elements used in tandem in an array.

Further discussions of curving composite probes are referenced in two additional technical papers, the first of which is "Improvements Of Ultrasonic Inspections Through The Use OF Piezo-Composite Transducers" authored by Gerard Fleury and Christian Gondard in May of 1995. Specifically in the area of reference to array probes, the article speaks to the regrouping of the transducer elements in the form of long and curved electrodes, but again is referring only to a multitude of individual elements used in tandem in an array, as shown in FIG. 7, which accompanied the technical paper. The left hand portion of FIG. 7 shows a completed transducer with cabling and black face material while the right hand portion shows an artists rendering of the multiple curved composite elements use to manufacture the finished product.

And the second being the Article "Use of Flexible Ultrasonic Arrays in Inspection," published in March 1999 and authored by Jocelyn Langlois, outlines forming a flexible transducer array by using a multitude of small elements as contemplated in the Splitt publication. Specifically, in the Langlois article an ultrasonic array is discussed with 1024 0.250"×0.250 transducer elements arranged in an 32×32 element matrix, vacuum coupled to a 12 inch diameter pipe. Although the application contemplated in this article differs vastly from OCTG tubular inspection, the desire to curve probes using multiples single elements and the advantages that can be realized are noteworthy.

Longitudinal Flaw Inspection

The inspection for longitudinal defects, oriented along the axis of the tube presents a whole new set of parameters and problems as opposed to wall thickness and transverse inspection, as were previously discussed and depicted in FIGS. 3 and 6. This is due to the relationship of the incident angle of the ultrasonic wave striking the curvature of the tube, and the adverse effects that slight movement of the probe in relation to the part being tested has on the incident angle and in turn the refracted inspection angle of the desired 45 degrees.

In the case of longitudinal flaw inspection, where the tube radius becomes a factor, this is not the case as shown in FIG.

Figure 8:
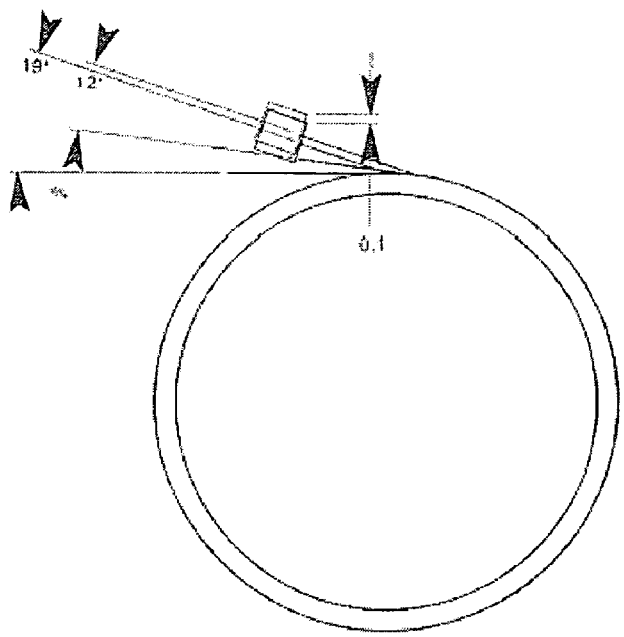
FIG. 8 is a drawing illustrating a sensitivity to change of the longitudinal inspection transducer before drastically altering the desired incident and refracted angles.

8. FIG. 8 shows the sensitivity to change of the longitudinal inspection transducer, with an associated upward movement of only 0.100", before drastically altering the desired incident and refracted angles. In this example, the 19 degree incident angle would result in the desired 45 degree refracted angle, while the 12 degree incident angle would alter the refracted angle by 17 degrees with a resultant refracted angle of 28 degrees, which would effect such a drastic change to inspection amplitude results that this is not only undesirable, but unacceptable to OCTG tube inspection. In fact, this phenomenon negates even the possibility of encircling the tube with, for example, 0.500" elements as we have used for demonstration on both the wall thickness and transverse inspection methods. This has been a major factor to the advent and maturing of phased array technology, which uses much smaller probes and actually "steers" the sound beam to compensate for this attribute of the ultrasonic longitudinal defect inspection method.

U.S. Pat. No. 4,195,530 to Ross et al. (the "'530 patent") describes an ultrasonic device for the inspection of a longitudinal weld in a tubular product. The transducer technology discussed in detail in the current invention, namely piezo-composite probes, was not in existence in 1980 when the '530 patent was issued. Given the advances in transducer manufacturing and the beam characteristics that are possible with curved composite probes, the theory of the '530 patent can now be applied to full body ultrasonic inspection as opposed only the inspection of a small area of a tubular as previously envisioned, namely a weld seam.

As is shown FIG. 9, a curved composite transducer can be developed for a range of tubular diameters (in this example, one length and radius transducer capable of inspection of sizes from 9.625 to 13.375) with various transducers being fabricated based primarily on radius and length to cover identified size ranges of OCTG for optimum coverage with a minimal number of transducer configurations. As the drawings of FIG. 9 depicts, on diameters of 13.375 and 9.625 pipe, a transducer with a radius of 7.188 inch and a length of 3.758 inch, the incident angles of 19 degrees in water, which in turn produces a refracted 45 degree angle in the pipe being inspected, provide 3.497 inches of surface coverage on the large pipe and a 2.516 inch of surface coverage on the smaller 9.625 inch pipe. For each pipe diameter there can be determined an optimum transducer as defined by radius and length that is best suited for a specific pipe diameter when inspecting for longitudinal flaws. As demonstrated in the top drawing of FIG. 9, it is possible to select transducer properties that can apply to a range of diameters while still achieving the desired properties including incident angle, water path, etc.

Figure 10:
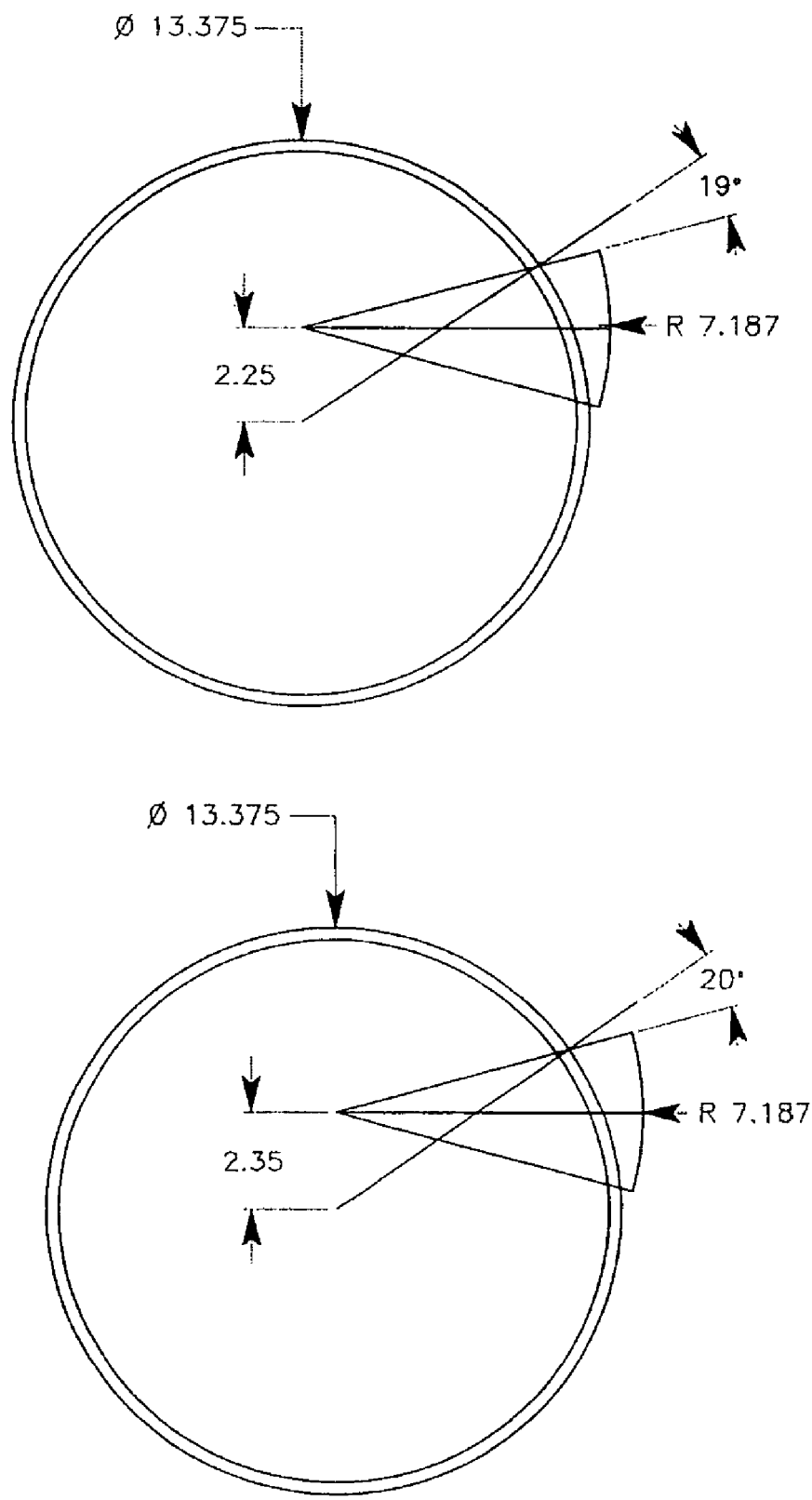
FIG. 10, is a drawing illustrating a smaller incident angle change over the prior art.

Any changes to the incident ultrasonic beam angle effects the refracted inspection angle in the part being tested. FIG. 10 illustrates that the current invention incorporates a method much better to the prior art method described in FIG. 8, in that comparable changes in the incident angle in the proposed method do not result in near the adverse effects inherent to the current technology. FIG. 8 demonstrated that a displacement of 0.100 inch with a conventional probe caused 7 degree variance in the incident angle. However, in the present invention an identical movement of the ultrasonic probe results in only a 1 degree incident angle change. The present invention is more forgiving relative to the pipe centering and inherent shoe wear during the ultrasonic inspection process.

While it is taught in the '530 patent that "any dimension beyond this minimum (length) is excess and serves no useful function. Since the cost of fabricating the ultrasonic transducer surface increases as the size of the transducer increases, the minimum dimension should not be exceeded."

As is demonstrated in FIG. 9, when considering full 100% coverage of the tube body, this excess which in the '530 patent is deemed undesirable, in the current invention, excess length can actually work as an advantage as it allows for a single radius and length of curved element to be used over a range of diameters, thereby actually reducing the overall cost and number of transducers needed for the final full body inspection unit.

As the current invention's goal is 100% coverage of the tubular being inspected, in all the required inspection orientations including wall thickness, transverse, and longitudinally oriented defects, the theory outlined in '530 patent for the isolated inspection of a small segment of the tube circumference for longitudinal flaws, must be expanded upon to achieve the desired 100% coverage necessary for full body ultrasonic inspection for longitudinal defects. The current invention addresses this shortcoming in the following manner, as depicted below in FIG. 11.

Figure 11:
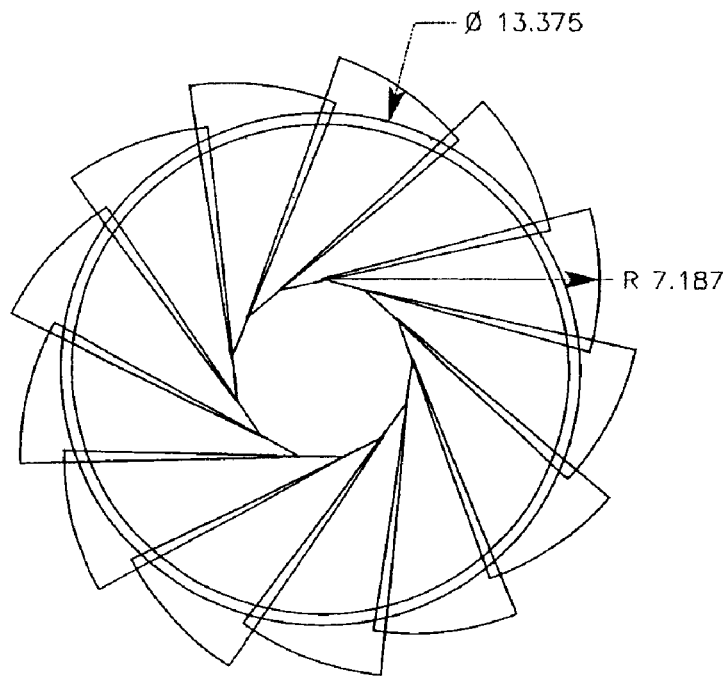
FIG. 11 is a drawing illustrating full 100% coverage of a tubular with a 13.325" diameter can be obtained using only thirteen ultrasonic channels and transducers.

FIG. 11 illustrates that by using the inspection method of the current invention, full 100% coverage of a tubular with a 13.325" diameter can be obtained using only. thirteen ultrasonic channels and transducers. This number would then be doubled, to insure coverage in both the clockwise and counterclockwise directions. The transducers are shown with a radius of 7.187".

Figure 12:
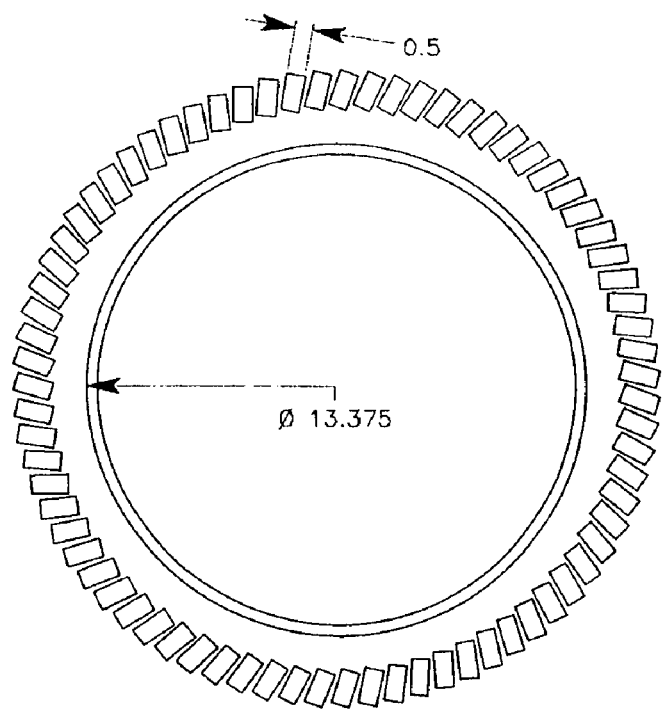
FIG. 12 is a drawing illustrating the use of prior art conventional technologies on tubular. with a diameter of 13.325" assuming an effective beam width of 0.500"

To achieve similar coverage using current conventional technologies, on the same diameter pipe and assuming an effective beam width of 0.500" the transducer configuration would be as depicted in FIG. 12. Though as previously discussed above, the sensitivity to change of incident angle relative to longitudinal flaw inspection negates even the possibility of encircling the tube with, for example, 0.500" elements as we have used for demonstration on both the wall thickness and transverse inspection methods.

It would require a total of seventy-five channels and transducers, with the associated costs, to achieve the 100% overlapping coverage achieved with only 13 channels and transducers as embodied in the current invention. To reiterate, this 75 channel total would be doubled to achieve the required the coverage in both clockwise and counterclockwise directions. At the conservative cost of $3,000.00 per ultrasonic channel listed in the chart, this results in a cost reduction of $186,000.00 which in turn would be doubled for both clockwise and counter-clockwise inspection.

Thus far, all calculations and discussions surrounding the current invention envision the transducers being mounted inside a water "stuffing" box with the tubular being transferred axially through the center of. the circular rings of probes. It will be apparent to those versed in the art that the embodied invention will also work using the contact method whereby the curved transducers are affixed to a wedge, the opposite dimension of which is machined to a radius to match the curvature of the tube being inspected. This is true for the wall thickness, transverse, and longitudinal portions of the present invention.

Figure 13A:
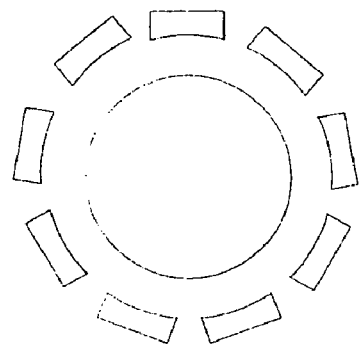
FIGS. 13A-13E are drawings illustrating the use of five sets of transducers utilized in the current invention.
Figure 13B:
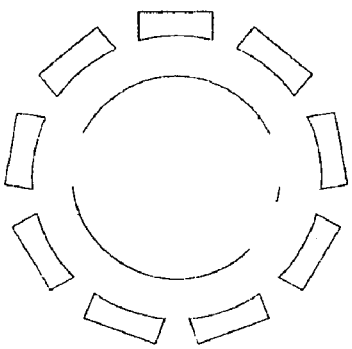
Figure 13C:
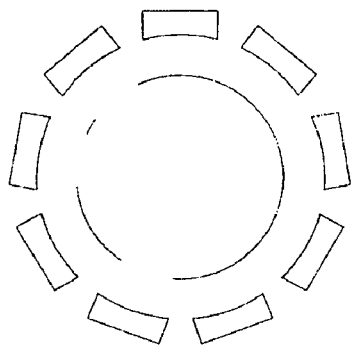
Figure 13D:
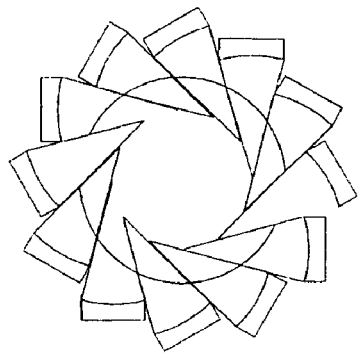
Figure 13E:
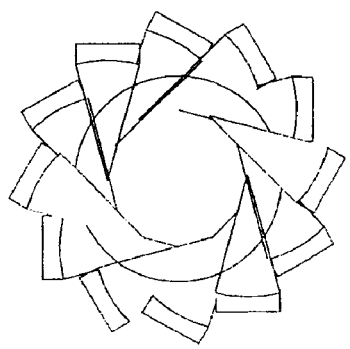

To summarize, the totality of required transducer rings envisioned in the current invention consist of the five sets pictured in FIGS. 13A-13E. FIG. 13A is a set of transducers to monitor the transverse leading portion of the pipe. FIG. 13B is a set of transducers to monitor the wall thickness of the pipe providing 100% coverage. FIG. 13C is a set of transducers to monitor the transverse trailing edge of the pipe. FIG. 13D is a set of transducers to monitor for longitudinal in the clockwise direction. FIG. 13E is set of transducers to monitor for flaws in the counter-clockwise direction.

It is also important to note that the specially designed curved composite transducers contemplated for use in the current invention also apply to the currently used technologies, namely helical advance, overhead gantry, and rotary head ultrasonic systems. If the probes outlined herein are incorporated into a conventional inspection unit, the same advantages relative to fewer channels and higher speeds still apply.

Figure 14:
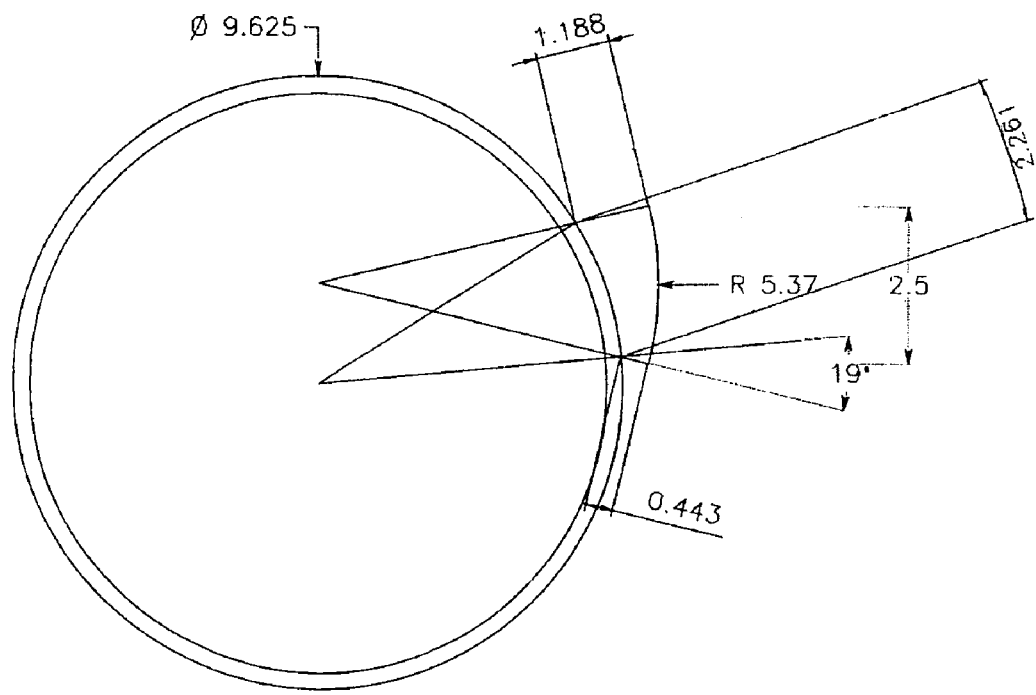
FIG. 14 is a drawing illustrating an embodiment of the present invention showing transducer beam coverage.

As an example of these inherent advantages, the transducer depicted in FIG. 14 will be used for calculation purposes, specifically the beam coverage at the 9.625 diameter pipe surface that is measured at 2.261". For calculation purposes, a 2.00" coverage at the pipe surface will be used to determine coverage per array. It should be noted that the transducer face, is mounted close to the pipe surface to capitalize on the increased coverage capabilities at the "base" of the triangle. The delay line (water, rexolite, lucite, etc.) from the top edge to the bottom edge of the embodied transducer ranges from 0.443" to 1.188", well within the range of conventional units currently in use that employ the varied methods of coupling the transducer to the tube, common to those in the industry.

An inherent shortcoming of the embodied invention is that by utilizing the described method for longitudinal flaw detection, the location of a flaw indication, relative to the internal diameter (ID) or outer diameter (OD) surface of the tube, cannot be determined as it can with the currently used technologies previously outlined, which typically use separate flaw "gates" to monitor the internal and external surfaces and help identify the location within the tube body wall, relative to the ID and OD surface. This shortcoming is due to the variance in the delay line between the face of the transducer and the surface of the tube being tested which in turn cause signal return time differences across the face of the probe.

The increased productivity and lower cost of the embodied ultrasonic inspection system substantially offset the disadvantage of not being able to achieve ID/OD differentiation. Most importantly, this minimal variance in water path does not detract from flaw detectability or unit performance overall, from a quality of inspection perspective.

If however this ability to differentiate ID and OD indications is a requirement in a particular environment, another aspect of the current invention is the ability to use the transverse and wall thickness sub-systems of the overall unit to make use of the advantages these methods have as stand alone components in terms of production levels and lower costs. It was previously outlined how these two sub-systems could perform as viable products on their own merits, in the areas of wall thickness measurement and used drill pipe inspection. The transverse and wall system could be coupled with, for instance, a rotating head ultrasonic inspection scheme, but with the added advantage of having all the ultrasonic channels associated with the rotary head focused solely on longitudinal flaw inspection. By using this approach, and depending on the number of available channels and the associated channel configuration, the speed of a rotary UT head could be increased dramatically as further outlined below.

Figure 15:
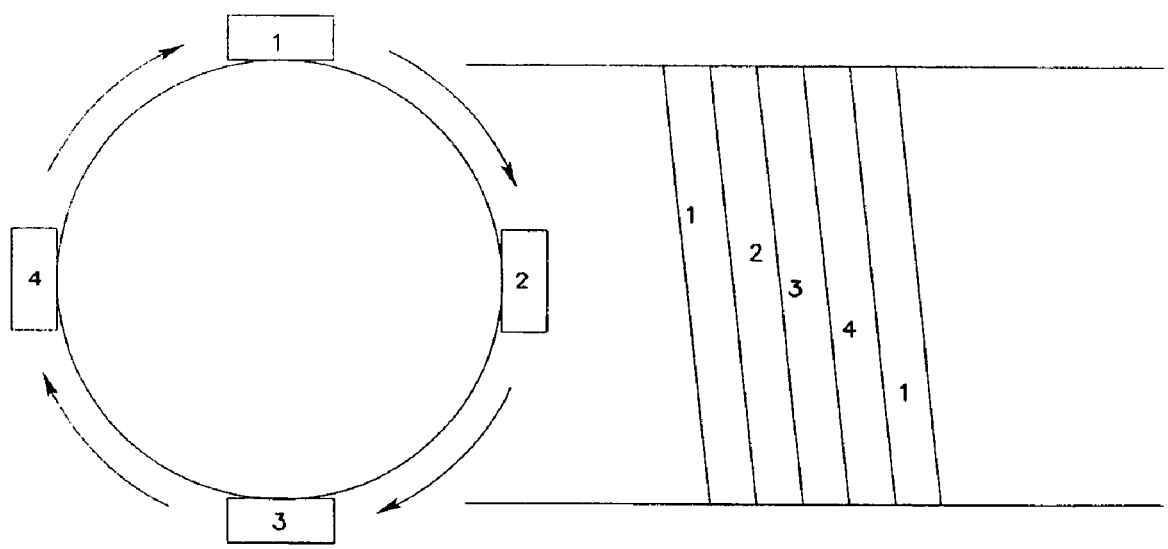
FIG. 15 is a drawing illustrating an embodiment of the present invention.

Rotary heads common to the industry typically use four inspection sensor holders positioned equidistant around the tube circumference. As shown by the helically sectioned pipe in FIG. 15, a transducer in each inspection shoe has a corresponding complementary transducer with the same properties and position within the individual shoes. The rotational speed and axial feed rate are adjusted to achieve the desired and required effect of 100% overlapping coverage when the multiple inspection sensor holders work in concert as the tube is inspected.

Figure 16:
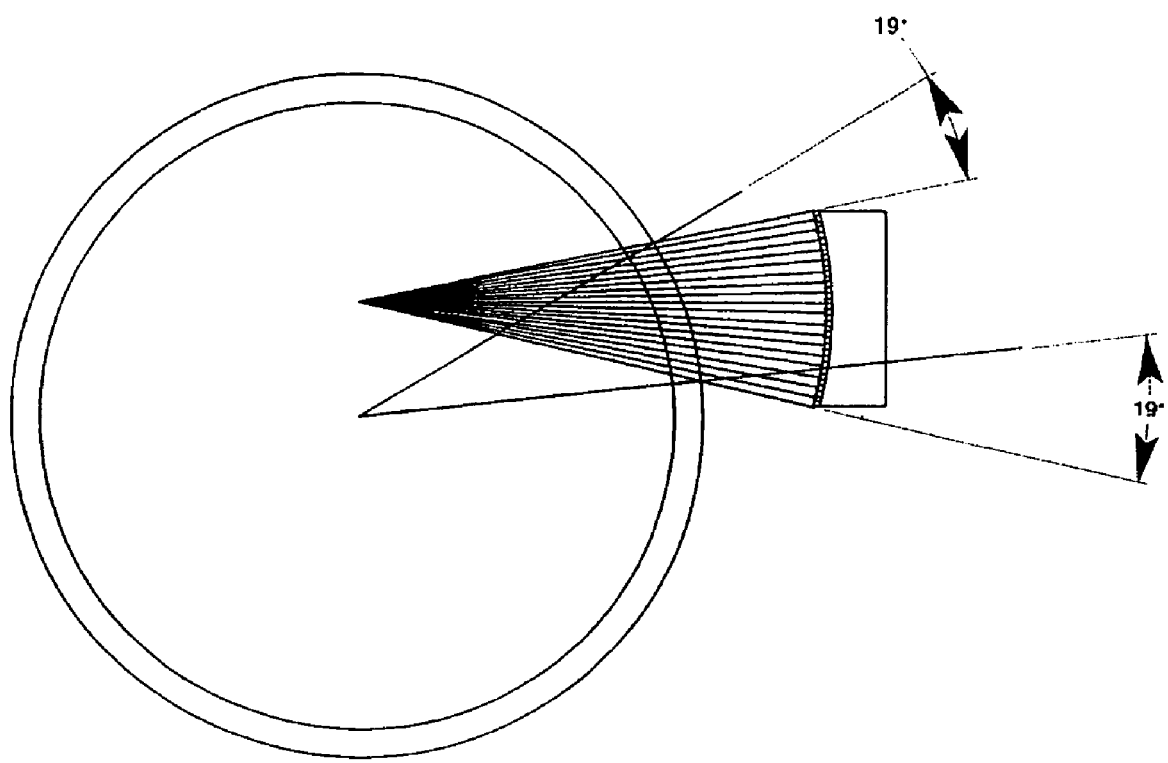
FIG. 16 is a drawing illustrating a phased array transducer.

If one takes a typical rotary head unit with a plurality of transducer arrays as described in FIG. 4 and further in FIG. 16, the resultant rotary head unit would have two leading and two trailing transverse arrays as in FIG. 4, each capable of producing a 2.873" helical advance mounted in opposing test shoes 1 and 3. When the rotation head speed and the pipe forward line speed are set to produce the desired 100% coverage, these two opposing shoes would produce a combined helical footprint or advance per revolution of 2.873" times 2, or 5.746" per revolution.

To perform the entire test as dictated by the API specifications longitudinal and wall thickness flaws must also be detected with additional test transducers and electronic channels. For longitudinal inspection, this scheme would be identical to that used for the transverse inspection, with two primary differences, the two 8 channel clockwise and counterclockwise arrays would be positioned to look around the circumference of the pipe and would be located in opposing shoes (as in FIG. 16) two and four with the resultant helix for the longitudinal also being 5.746" per revolution.

For the remaining wall thickness inspection, the arrays are typically spread evenly among the test shoes 1 through 4, as unlike transverse and longitudinal, wall inspection is performed with the transducer sound beams directed perpendicular to the pipe surface, negating the need for leading and trailing probe in the case of transverse inspection, or clockwise/counterclockwise opposing arrays in the case of longitudinal. So for wall thickness inspection, each shoe 1 through 4 would have four wall thickness transducers with the resultant helical advance being equal to the longitudinal and transverse arrays, or 4 transducers per shoe with an ultrasonic footprint or effective beam area per 4 transducers of 2.873 divided by 2, or 1.437" per shoe each of the test shoes one through 4, for a total wall thickness coverage area of 1.437" times 4, or 5.746" per revolution, identical to the longitudinal and transverse combined arrays.

A marked improvement in productivity and pipe throughput to this standard rotary style ultrasonic unit can be obtained by combining this standard technology with components from the proposed invention, namely the circular wall thickness and transverse arrays, which as discussed, are not as sensitive to variances in distance from the pipe surface as in the case of the longitudinal inspection system. This would be accomplished by adding a non-contact, non-rotating encircling transverse and longitudinal inspection ring immediately prior to the existing rotary head mechanics in a water "stuffing" box, or other industry accepted method of ultrasonic coupling previously discussed. The test heads 1 through 4 remaining on the standard rotary head would be modified whereby all previous transverse and longitudinal transducers would be dedicated only to longitudinal inspection, with all ultrasonic transducers in the rotary head, a total of 64 channels or 16 per shoe, positioned to inspect around the pipe circumference to detect longitudinal oriented defects.

So for transverse inspection, portions of the array depicted in FIG. 4 would be split among the four surrounding, equidistant shoes as follows, 4 per shoe (2 leading and two trailing). This assumes a total number of transducers being dedicated to transverse flaw inspection to be double the amount in FIG. 4, to allow for leading and trailing inspection. In this configuration, a typical rotary head unit, with the addition of two components from the proposed invention, would be capable of inspection speeds twice as fast as before due to an increase in helical advance from 5.746" up to 11.492" with only an incremental increase in channels as described with reference to FIGS. 13A, B, and C.

The novelty of this approach is that this can be achieved with no increase in the rotary head speed, (which is the limiting factor for production on this type of unit, i.e. the mechanical mass can only be spun so fast) could then be devoted to strictly longitudinal arrays as previously described.

Perhaps of even greater interest would be to couple a phased array longitudinal inspection system with the transverse and wall components of the current invention, but mount the individual phased array channels within a curved transducer case to duplicate the ultrasonic "wave front" as the composite transducers embodied in the present invention. One of the features of phased array ultrasound is numerous ultrasonic channels per transducer case or housing. As previously mentioned, a single transducer housing could contain up to 256 individual transducer elements, all requiring individual electronic channels. As shown in FIG. 16, a phased array transducer, formed in this way and used in the described manner, provide not only the consistent angle of incidence as contemplated by the current invention, but also provide the ability to differentiate between ID and OD flaws, as modern phased array systems track flaw signal return on a per element basis, and can then perform calculations to make the determination of flaw location within the body wall possible.

Even though the benefits of using the proposed transverse and wall thickness components with, for example, a rotary head unit are obvious to one versed in the art, they pale in comparison to the advantages that these stand-alone systems can yield to a phased array full length tube inspection machine. By their nature, phased array systems are very expensive due to the high number of ultrasonic channels required to obtain 100% coverage, the high cost of related transducers, and high cost of coaxial signal cable among other factors. In fact, to date, the only axial feed (as contemplated by the current invention) phased array inspection system for large diameter pipe addresses only longitudinal and wall thickness inspection, with the inspection for transverse flaws being performed with an after market flux leakage system common in the industry. This course of action was due in part to the technological obstacles associated with phased array technology for the detection of transverse flaws, as well as the excessive costs associated with the number of channels that would be required to inspect for transverse flaws were the phased array method used.

Comparison of Old Technology and Present Invention

For calculation and comparison purposes, we will consider that no time is lost due to loading or unloading, gaps between successive tubes, mechanical breakdown, or paused in production of any kind. In essence, the tubes are run through "end to end."

It should be noted, that from a cost per channel perspective, a comparison of the embodied invention to currently used technologies is not feasible as the number of channels required in a conventional testing machine, to match the production rates of the described invention, are a moot point as mechanical restrictions preclude current methodologies from obtaining equal production possibilities.

Table 1 identifies certain parameters utilized for comparison of the present invention with prior technology.

TABLE 1

| | |
|---|---|
| Pulse repetition rate | 2.5 khz |
| Transducer element size | 0.625" |
| Effective beam 70% | 0.438" |
| Acceptable pulse gap | 0.040" |
| Number of transducers per array | 8 |
| Tube length | 50 ft |
| Coverage per array 8 X .438 = 3.50" | |
| Average cost per ultrasonic Channel | $3,000.00 |

The following Table 2 demonstrates a significant increase in productivity were it possible to design and manufacture such a system, requiring no rotation of the tube or test head.

TABLE 2

| | Crystal diameter | Effective beam | Pulse rate | surface speed |
|---|---|---|---|---|
| Pulse Gap Calculator | 0.625 | 0.438 | 2500 | 100 |
| | Rpm | Pipe diameter | pipe circ. | helical advance |
| Surface Speed | 199 | 9.625 | 30.22 | 3.5 |
| | Forward advance Feet per Minute | Tubes per hour | Tubes per 12 hour | |
| Prior Technology | 58 | 69 | 834 | |
| Present Invention | Feet per minute Potential axial speed | Tubes per hour | Tubes per 12 hour | |
| | 500 | 600 | 7200 | |
| | Current tubes per 12 hr turn | Potential tubes Per 12 hr turn | Percent production Improvement | |
| Production Comparison | 834 | 7200 | 863.5% | |

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for ultrasonic inspection of tubulars, said method comprising:
   providing a first circular array of composite transducers, said transducers having a proximate curved surface;
   passing a tubular past said first array, said tubular having an outer peripheral surface, wherein said outer peripheral surface has a radii of curvature, and said proximate curved surface has a radii of curvature greater than the radii of curvature of the outer peripheral surface; and
   inspecting for abnormalities in the tubular utilizing said transducers.

2. The method of claim 1, wherein the step of passing includes moving the tubular in a longitudinal direction past said first array without rotating the tubular in a circumferential direction.

3. The method of claim 1, wherein the step of providing includes maintaining said first array in a stationary position.

4. The method of claim 1, wherein said tubular has a wall thickness, and the inspecting step includes determining abnormalities in the wall thickness.

5. The method of claim 1, wherein the inspecting step includes determining abnormalities of a longitudinal flaw type.

6. The method of claim 1, wherein the inspecting step includes determining abnormalities of a transverse flaw type.

7. The method of claim 1, wherein the inspecting step includes utilizing shear waves for determining abnormalities of a longitudinal flaw type and transverse flaw type.

8. The method of claim 1, wherein said transducers are each a length of equal to or greater than 2 inches.

9. The method of claim 1, wherein said transducers are each a length of between 0.25 inches and 2 inches.

10. The method of claim 1, wherein said passing step includes maintaining the proximate curved surface of each transducer equi-distant from said outer peripheral surface of the tubular.

11. The method of claim 1, wherein the pipe has a diameter ranging from equal to or greater than 2 3/8 inches.

12. The method of claim 1, wherein the first array is adapted to detect variations in wall thickness.

13. The method of claim 1, further comprising the step of providing a phase array longitudinal inspection system having individual phased array channels and with multiple elements.

14. The method of claim 1, wherein the first array each include four or more transducers.

15. The method of claim 1, further comprising:
   providing a second and third array of composite transducers, said transducers having a proximate curved surface;
   wherein relative to a central longitudinal axis of the tubular, said transducers of the second and third array are angled 19 degrees in water to produce a 45 degree refracted angle.

16. The method of claim 15, wherein the inspecting step includes determining abnormalities of a transverse flaw type.

17. The method of claim 15, wherein the second and third array each include four or more transducers.

18. The method of claim 15, further comprising:
   providing a fourth and fifth array of composite transducers, said transducers of the fourth and fifth array having a proximate curved surface, the fourth and fifth array adapted to inspect for longitudinal flaws.

19. A system for ultrasonic inspection of a tubular, said system comprising:
   a first circular array of composite transducers, said transducers having a proximate curved surface with a radii of curvature greater than the radii of curvature of the outer peripheral surface of said tubular, wherein said circular array is adapted for inspecting for abnormalities in the tubular utilizing said transducers.

20. The system of claim 19, wherein the curved transducers are piezocomposite transducers.

21. The system of claim 19, further comprising a phase array longitudinal inspection system having individual phase array channels to form a curve.

22. The system of claim 19, further comprising a second and third array of composite transducers, said transducers having a proximate curved surface.

23. The system of claim 22, wherein said transducers of the second and third array are angled 19 degrees in water to produce a 45 degree refracted angle.

24. The system of claim 22, wherein the second and third array are adapted to inspect for abnormalities of the transverse flaw type.

25. The system of claim 22, wherein the second and third array each includes four or more transducers.

26. The system of claim 22, further comprising:
   a fourth and fifth array of composite transducers, said transducers of the fourth and fifth array having a proximate curved surface, the fourth and fifth array adapted to inspect for longitudinal flaws.

27. The system of claim 26, wherein the fourth and fifth array each includes four or more transducers.

28. The system of claim 19, wherein the first array each includes four or more transducers.

29. The system of any one of claims 19, wherein the first array is adapted to detect variations in wall thickness.

* * * * *